(12) United States Patent
Drevik et al.

(10) Patent No.: US 10,058,462 B2
(45) Date of Patent: Aug. 28, 2018

(54) MULTI FUNCTION WRAPPER

(75) Inventors: Solgun Drevik, Mölnlycke (SE);
Chatrine Stridfeldt, Hovås (SE);
Angelica Burvall, Bollebygd (SE)

(73) Assignee: SCA Hygiene Products AB, Gothenburg (SE)

( * ) Notice: Subject to any disclaimer, the term of this patent is extended or adjusted under 35 U.S.C. 154(b) by 424 days.

(21) Appl. No.: 12/299,394

(22) PCT Filed: May 3, 2007

(86) PCT No.: PCT/SE2007/050301
§ 371 (c)(1),
(2), (4) Date: Nov. 3, 2008

(87) PCT Pub. No.: WO2007/129978
PCT Pub. Date: Nov. 15, 2007

(65) Prior Publication Data
US 2009/0112174 A1    Apr. 30, 2009

(30) Foreign Application Priority Data

May 4, 2006 (WO) ................. PCT/SE2006/000539

(51) Int. Cl.
*A61B 19/02* (2006.01)
*A61F 13/84* (2006.01)
*A61F 13/551* (2006.01)

(52) U.S. Cl.
CPC .......... *A61F 13/5514* (2013.01); *A61F 13/84* (2013.01)

(58) Field of Classification Search
CPC ............ A61F 13/551; A61F 13/55105; A61F 13/5513; A61F 13/5514; A61F 13/5516; A61F 13/55175; A61F 13/84

USPC ......... 206/440, 438, 484, 204, 484.1, 484.2, 206/363, 570; 604/385.01–385.06
See application file for complete search history.

(56) References Cited

U.S. PATENT DOCUMENTS

| | | | |
|---|---|---|---|
| 2,834,459 A | 5/1958 | Rickard et al. | |
| 4,848,572 A | 7/1989 | Herrera | |
| 5,111,934 A * | 5/1992 | Morin | ............ 206/229 |
| 5,261,531 A | 11/1993 | Nieves | |
| 5,487,932 A * | 1/1996 | Dunshee | ............ 206/438 |
| 5,569,230 A | 10/1996 | Fisher et al. | |
| 5,702,379 A | 12/1997 | Preiss | |
| 6,010,001 A | 1/2000 | Osborn, III | |
| 6,350,931 B1 | 2/2002 | Martin | |

(Continued)

FOREIGN PATENT DOCUMENTS

| | | |
|---|---|---|
| EP | 0 350 924 A2 | 1/1990 |
| EP | 0 850 617 A1 | 7/1998 |

(Continued)

OTHER PUBLICATIONS

Form PCT/ISA/210 (International Search Report) dated Aug. 16, 2007.

(Continued)

*Primary Examiner* — Andrew Perreault
(74) *Attorney, Agent, or Firm* — Buchanan Ingersoll & Rooney P.C.

(57) ABSTRACT

A packing wrapper for an absorbent article, the wrapper having a protective layer. The wrapper also has a first functional layer attached to the protective layer giving the wrapper a multiple functionality.

21 Claims, 11 Drawing Sheets

(56) References Cited

U.S. PATENT DOCUMENTS

| | | | |
|---|---|---|---|
| 6,911,022 B2* | 6/2005 | Steger et al. | 604/385.06 |
| 2002/0156448 A1 | 10/2002 | Steger et al. | |
| 2003/0149417 A1 | 8/2003 | Kudo | |
| 2007/0038197 A1 | 2/2007 | Nijs et al. | |

FOREIGN PATENT DOCUMENTS

| | | |
|---|---|---|
| EP | 1 332 746 A2 | 8/2003 |
| EP | 1354575 A1 | 10/2003 |
| JP | 2003-290283 A | 10/2003 |
| RU | 2 285 649 C2 | 8/2005 |
| WO | 93/21878 | 11/1993 |
| WO | 00/76878 A1 | 12/2000 |
| WO | 03/034965 A2 | 5/2003 |
| WO | 03/053397 A1 | 7/2003 |
| WO | 2004/060416 A1 | 7/2004 |
| WO | 2004/105822 A1 | 12/2004 |
| WO | 2007/017844 | 2/2007 |

OTHER PUBLICATIONS

Form PCT/ISA/237 (Written Opinion of the International Searching Authority) dated Aug. 16, 2007.
Form PCT/IPEA/409 dated Jul. 7, 2008.
Office Action dated Sep. 23, 2010, issued by the Russian Patent Office in corresponding Russian Patent Application No. 2008147717 and English translation thereof.
Japanese Office Action issued Apr. 3, 2012, in corresponding Japanese Application No. 2009-509496, together with an English translation thereof.
Notice of Acceptance issued May 30, 2013, in corresponding Australian Application No. 2007248966. (3 pages).

* cited by examiner

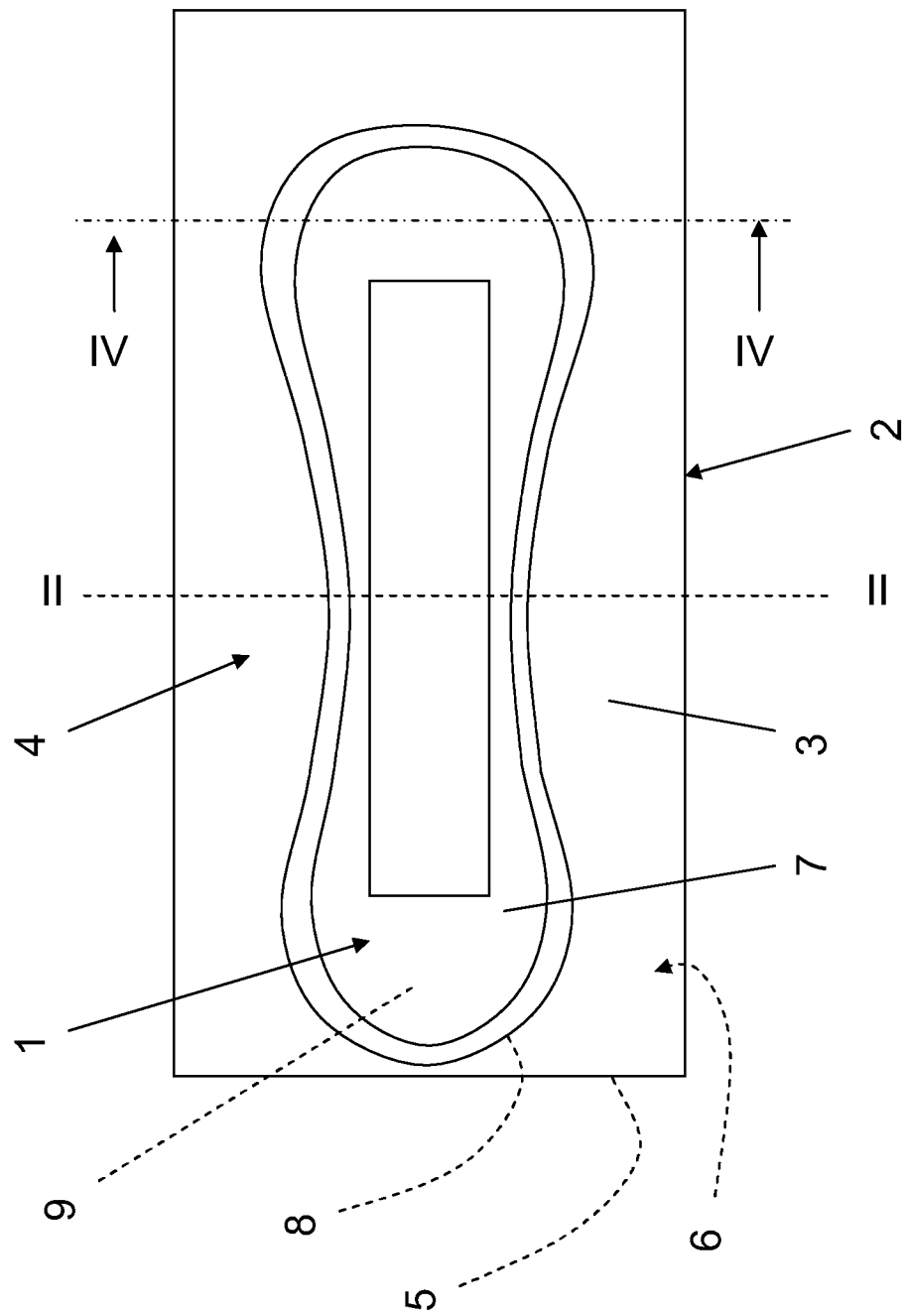

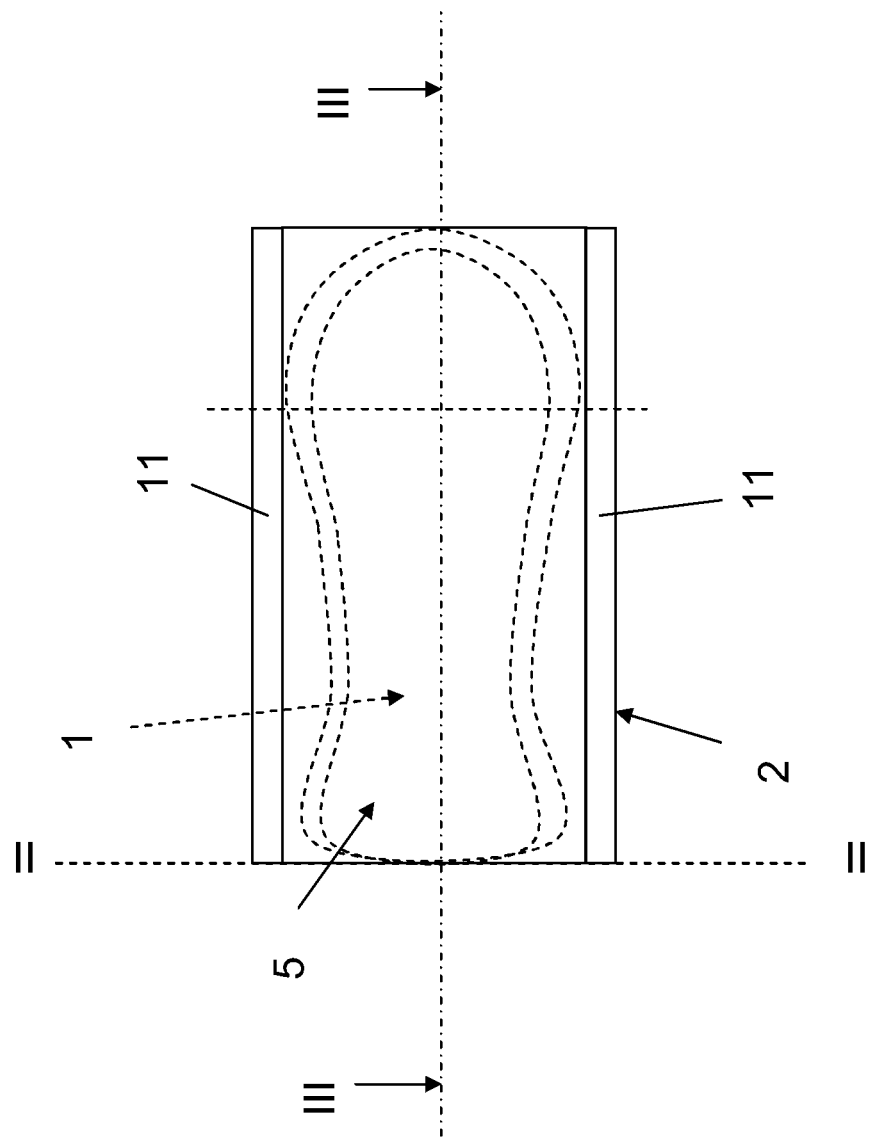

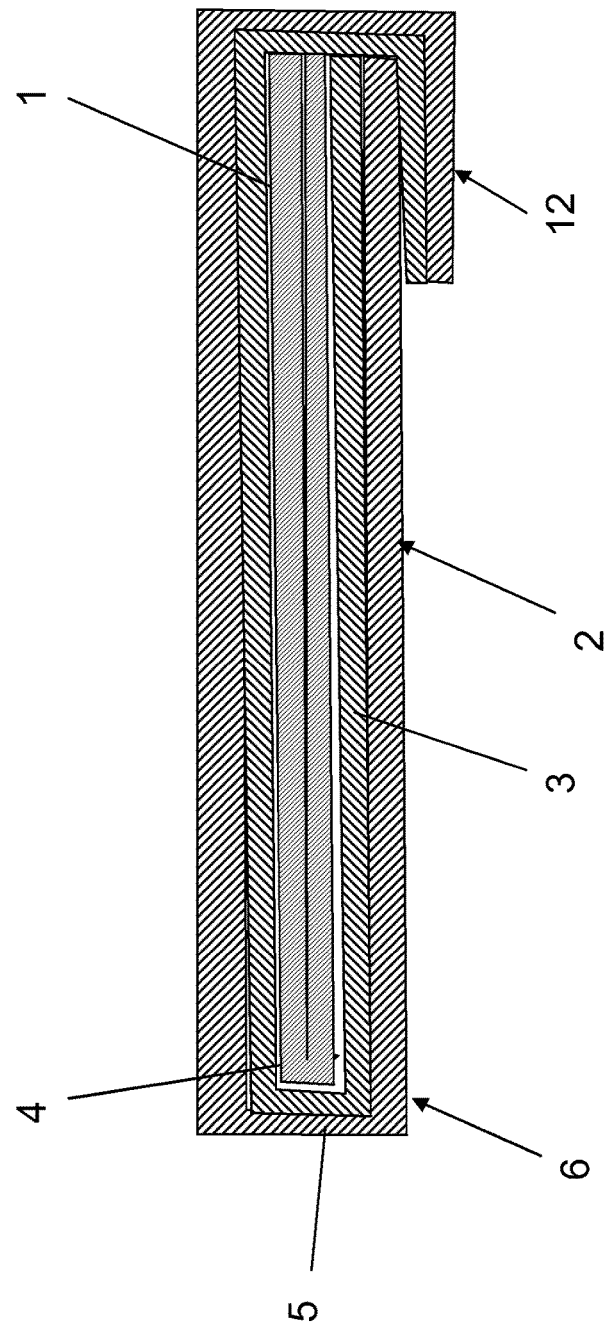

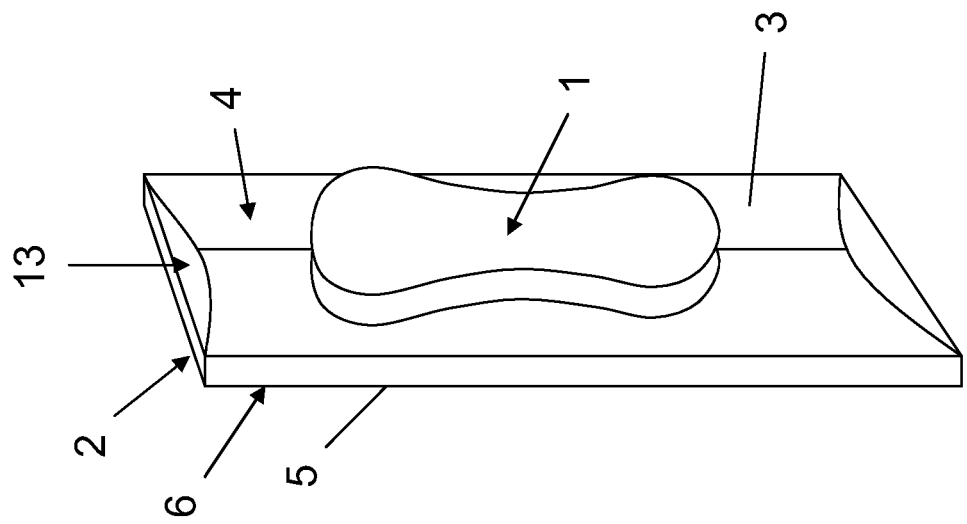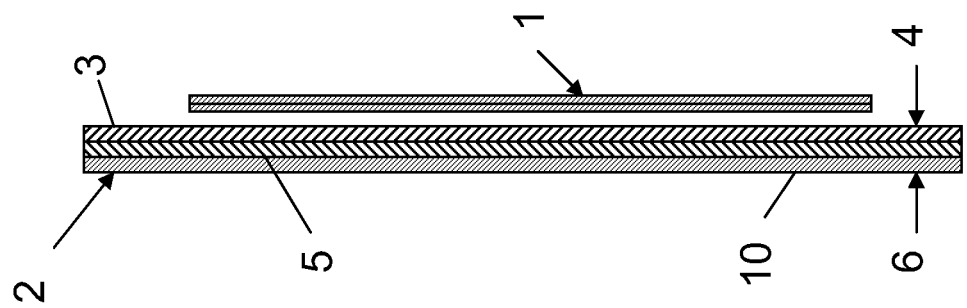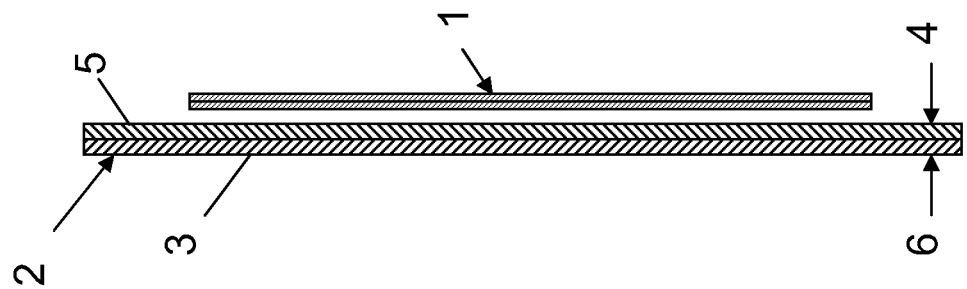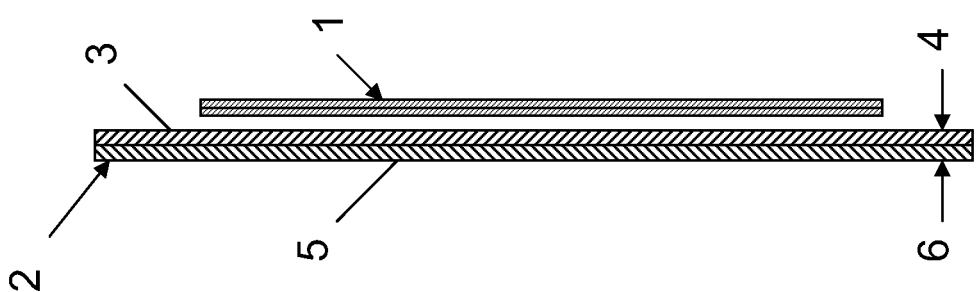

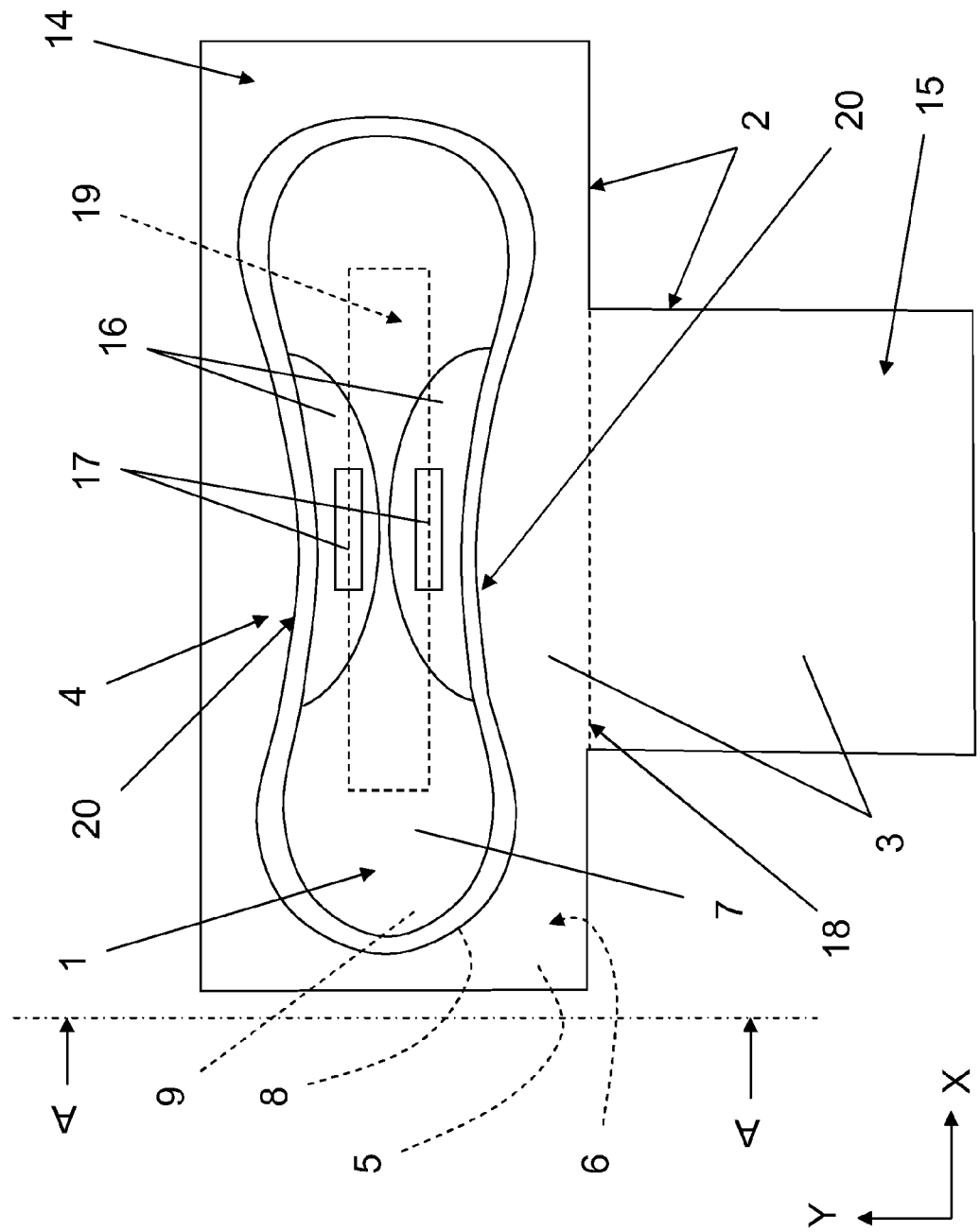

MULTI FUNCTION WRAPPER

PRIORITY

This application is a national stage application of PCT/SE2007/050301, filed 3 May 2007, which claims priority to PCT/SE2006/000539, filed 4 May 2006.

TECHNICAL FIELD

The disclosure refers to a wrapper for a packed absorbent article. The wrapper comprises a protective layer.

BACKGROUND ART

It is advantageously known to pack a single absorbent article of the kind referred to as in a packing wrapper. In this way, small, handy packs are obtained, which can easily and conveniently be kept in a handbag or in a pocket and from which an article can be removed when necessary. Such individual packs ensure that the article is protected against soiling and crumpling until use and are therefore greatly appreciated by users. With suitable design of the packing wrappers, these can also serve as wrappers for used articles, which can thus be disposed of in a hygienic and aesthetically acceptable way.

The most common type of material used as packing wrappers for absorbent articles of the kind described is thin coloured plastic films, which are normally tightened relatively firmly around the absorbent article located inside the packing wrapper.

When a user changes the used absorbent article for a new fresh absorbent article, the user normally wants to clean the genital area from any bodily fluids remaining in that area after removal of the used absorbent article. Furthermore, the user may also want to clean a sitting surface or the like before sitting down. In both cases the user then uses a cleaning means such as a napkin or a piece of paper for the cleaning. A problem occurs when such a cleaning means cannot be obtained because the environment does not supply the cleaning means and the user has forgotten to bring a cleaning means. The new absorbent article then has to be put in place without the genital area having been cleaned and the user may have to stand up instead of sitting down.

A need therefore remains for an improved handling during change of an absorbent article where the above problem is removed.

OBJECTS AND SUMMARY

The disclosure is intended to remedy the above problem by introducing a wrapper for an absorbent article where the wrapper comprises a protective layer and is characterised in that the wrapper comprises also a first functional layer attached to the protective layer giving the wrapper multiple functionality.

An advantage of the disclosure lies in the multiple functionality of the wrapper which both protects the absorbent article and always gives a user access to a functional layer, that can be used as a cleaning means or the like, when switching from a used absorbent article to a new absorbent article since the cleaning means is a part of the wrapper in the form of the first functional layer and is therefore always at hand.

Here, absorbent article refers to sanitary articles used in an undergarment for protection against bodily exudates such as menstrual fluids and urine and other liquids emanating from orifices in the genital area. Absorbent articles thus refer to incontinence articles for men and women as well as menstrual protection articles for women. A typical absorbent article comprises a sandwich structure comprising a liquid pervious topsheet, a liquid impervious backsheet and an absorbent body therebetween.

In order for the understanding of the concept "layer", the following theoretical model defines a layer as a thin body comprising one or more materials having two main opposing surfaces extending essentially parallel in two dimensions and having essentially one or several predetermined and predominating properties. The property may be, for example, absorbent, or liquid impermeable, or hydrophilic, or hydrophobic etc. In use the layer is formed around a three dimensional object and conforms to the theoretical model only when being flattened out in the two dimensions.

The wrapper may be made from two separate layers by attaching the first functional layer to the protective layer over a part of or the entire main surface. The first functional layer may here be a body made from an absorbent material and the protective layer may be a body made from a liquid impervious material. The absorbent material may be liquid absorbent and/or particle absorbent or adsorbent.

The protective layer may also be coated onto the first functional layer. Coating refers to a method where a substance/material that cannot be supported by its own structure, for example a material in liquid form, uses the first functional layer as a support structure. For example, the material intended to form the protective layer is applied onto the first functional layer at one temperature and secured to the first functional layer by hardening the material by lowering the temperature. However, coating is known from prior art and may be made in a number of known ways.

In another embodiment, the protective layer may be made by impregnating partly or wholly one of the opposing surfaces of a material layer and where the first functional layer is formed in the other opposing surface not being impregnated. Impregnating refers to the use of a substance rendering the surface and an additional part in a thickness direction of the material layer the protective features desired for the protective layer, for example waterproof and/or dirt repellent. Here, additional parts refer to that part of the material layer being affected by the impregnating substance by, for example, diffusion, i.e. the impregnating substance's ability to be transported into the material. The impregnation should not be allowed to strike through the material layer since this could destroy the functional feature of the first functional layer, i.e., e.g. the absorbent properties. In this embodiment the protective layer comprises that part of the material layer having been affected enough to render the material layer protective and the first functional layer comprises the opposing surface and that part of the material layer not affected by the impregnation.

The protective layer and the first functional layer may be made from different fibrous materials mixed such that a first fibrous material is predominating in one of the wrapper surfaces and gradually decreases towards the opposing surface where a second fibrous material is predominating. The first fibrous material may form the protective layer and the second fibrous material the first functional layer, or the opposite, and the predominating features may be any of the above stated predominating properties.

The first functional layer is positioned on that face of the wrapper facing the absorbent article (hereinafter called the inside) or on that face of the wrapper facing away from the absorbent article (hereinafter called the outside).

In one embodiment of the disclosure a second functional layer (hereinafter called second functional layer) is positioned on the opposite side of the wrapper with reference to the first functional layer. The advantage of this embodiment lies in that the user has two functional layers that can be used. For example, the second functional layer may be positioned on the outside of the wrapper and may comprise an absorbent wiping material that can be used for wiping off a soiled surface that may need cleaning before use, for example a sitting surface of a toilet, or a mirror, or a bath tub etc. The first functional layer may be positioned on the inside of the wrapper and may comprise a wiping material and/or a suitable additive which can be used by the user for cleaning a genital area of a user and/or for transferring the additive to the genital area.

The second functional layer and the protective layer may be formed in relation to each other in the same manner as described above for the relationship between the first functional layer and the protective layer. Hence, the protective layer may be coated onto the second functional layer or the second functional layer and the protective layer may form separate layers attached to each other.

Even if it is advantageous for several reasons to pack single absorbent articles of the kind referred to in the introduction in individual packing wrappers, it is possible to use the inventive wrapper when packing more than one absorbent article. The user then has at least one opportunity to use the first functional layer or, if the case may be, both the two functional layers.

Furthermore, the inventive wrapper may also be used as a main wrapper for packing a number of absorbent articles each being packed in the inventive wrapper. The advantage of this idea lies in that the user is provided an additional multiple functioning wrapper according to the disclosure when breaking the main wrapper. The main wrapper may, for example, be used for cleaning the sitting surface of a toilet and the single wrapper is then used for cleaning the genital area.

In one embodiment of the disclosure the first functional layer is applied on the inside of the wrapper and the first functional layer comprises an additive in the form of an active substance for treatment of the body, for example a lotion, or an anti-bacterial substance, or a moisturiser, or soap, or an odour-control agent, or a perfume, or any other suitable substance or active agent.

EP 0850617 teaches different classes of odour-control agents known in the art according to their different mechanisms of action for use with disposable absorbent articles. A first class of odour-control agents is constituted by compounds that interfere with the bacterial metabolism, in order to avoid or to reduce the production of malodorous metabolites from the body fluids; such agents can be bactericides or bacteriostats and are typically available as water-soluble compounds. A second class of odour-control agents comprises those compounds, typically in particulate form, that are capable of adsorbing within their structure the odoriferous substances, both those already present in the body fluids as such and those produced by the bacterial metabolism. Another class of odour-control agents comprises perfumes that essentially mask the unpleasant odours; moisture-activated encapsulated perfume particles can also be used, in which the perfumes are released only when the material is wetted, to provide their action during the use of the product, and to optionally avoid interaction with other odour-absorbing agents before the product is used, if such a combination is actually used as the odour-control means. A broader distinction can be made among the odour control agents known in the art. Some odour control agents are active preferably in dry conditions, that is, when substantially not wetted by absorbed fluids. Moreover, negative influence of liquid is even more enhanced when the pH conditions are far from neutrality, which is most likely to occur in structures for absorbing body fluids, owing to the degradation of the fluids themselves. Other odour control agents perform their action in solution, and therefore must be wetted by the absorbed fluid. Odour control agents belonging to the above mentioned first class are typically active in solution; this is true for some perfume substances too, for example the moisture-activated encapsulated perfumes. On the contrary, odour control agents of the second class are typically active towards gaseous odorous compounds related to the absorbed fluid by means of e.g. an adsorption mechanism, and therefore better perform their action in substantially dry conditions. Bearing in mind this distinction, any odour-control agent known in the art that can be suitably incorporated in absorbent structures for absorbing body fluids, or any suitable combination thereof, can be used in the laminated absorbent structures of the present disclosure, to provide the article which incorporates this structure as the absorbent element, or at least as part of it, with the benefit of controlling the odours associated with absorbed body fluids.

The absorbent article may in the case of using an active substance have a release layer being positioned on the liquid pervious topsheet of the absorbent article. Alternatively, only a part of the wrapper constitutes the first functional layer and the first functional layer is positioned against the liquid impervious backsheet of the absorbent article. In this embodiment the moist first functional layer will not impart moisture to the absorbent body since the backsheet is used as a cover.

WO 2003/034965 teaches skincare agents that may be used in the first and/or the second functional layer of the present disclosure, for example a pH-regulating substance, antimicrobial substances, glucocorticoids, antiviral agents, probiotic microorganisms, enzyme inhibitors, and anti-inflammatory substances.

WO 2004/060416 teaches additives suitable for use with a hygiene tissue. The additives may be used alone or in combination in the first and/or the second functional layer according to the disclosure. The additives are: lactic acid producing bacteria selected from the genera *Pediococcus, Lactococcus, Lactobacillus* or mixes thereof; a lipid such as olive oil, canola oil, coconut oil, palm kernel oil, peanut oil, soy bean oil, dimethicone, paraffin oil and petrolatum; an additive in the form of calcium chloride; pH buffering agents (such as weak organic or inorganic acids such as lactic acid, ascorbic acid, citric acid or boric acid); perfume; antioxidants; hydrocortisone or other anti-inflammatory steroids; anti-freezing agents (such as skim milk, glucose, glutamate and glycerol); nutrients (such as amino acids, peptides, nucleic acid derivatives, vitamins, salts, fatty acids, glucose, fructose, ribose, maltose, and lactose); and/or one or more optional cleaning additives such as emollients, emulsifiers, tensides such as non-ionic, amphoteric and anionic surfactants, moisturisers, pH-regulating agents, chelating agents, viscosity modifiers, antimicrobial agents, preservatives and fragrances.

The first or second functional layer may also comprise an active substance suitable for cleaning non-bodily soiled surfaces, for example an anti-bacterial agent or the like.

The first and/or the second functional layer may comprise an active substance which can be activated by contact with water or heat or in contact with air. The activation may also be done by mechanical action, for example breaking of a capsulated unit.

In one embodiment of the disclosure, the wrapper comprises a loosely attached first functional layer forming a pocket between the protective layer and the first functional layer. The user may stick a hand or parts of a hand into the pocket and may use the wrapper as a glove with a first and/or a second functional layer for the purpose of wiping a surface and/or transferring an additive. The pocket may also be used when disposing a used absorbent article. The absorbent may then be put into the pocket before disposal which gives the advantage that the used sanitary napkin may be stored in a discrete, hygienic and odourless manner. Furthermore, a user may stick a hand into the pocket and grab an object, for example the absorbent article, with the wrapper as a glove and then turn the pocket inside out in order to store the object in the inverted pocket.

The wrapper may also comprise two protective layers loosely attached to each other forming a such that a protective layer is positioned on either side of the hand when using the pocket, i.e. the wrapper may comprise two protective layers being attached only partly and separated so that the pocket is formed. The user then has the first and/or the second functional layer to be used according to the above without the hand being soiled.

The wrapper may also comprise two separating layers between the two protective layers. The two layers separate the two protective layers. The separating layers may be attached in the wrapper so that the wrapper may be split into two units between the separating layers. The units each comprise a first and/or a second functional layer, a protective layer and a separating layer respectively. The separating layers may be attached to the protective layers only partly and separated so that each unit comprises a pocket that can be used for using each unit as a glove.

The wrapper may also comprise several additional layers of the first and/or the second functional layer. The additional layers may be removed one at a time from the wrapper and may be used individually by the user.

The wrapper may also comprise a release layer laminated onto the first and/or the second functional layer. The release layer may function as a protective layer and uncovers the respective first and/or the second functional layer. Furthermore, the release layer may also be used for activating the active substance in the first and/or the second functional layer when removed.

The protective layer is advantageously water and/or moisture impermeable in order to keep the absorbent article dry. The protective layer may also have low friction and may be dirt repellent.

The first and/or the second functional layer may have an extension less than the protective layer, i.e. they need not extend to the peripheral edge of the protective layer. Furthermore, the first and/or the second functional layer need not be permanently attached to the protective layer, but may be removably attached to the protective layer, i.e. the layers may be separated by the user.

Below is a non-exhaustive list of materials of suitable materials. In the example the first functional layer faces the absorbent article in the packing, i.e. is placed on the inside of the wrapper. The second functional layer is thus placed on the outside of the wrapper:

1. The wrapper comprises the first functional layer coated with a substance making up the protective layer:
   1a. The first functional layer may comprise:
     An air-laid tissue
     A nonwoven being spunbond, metlblown or carded, etc
     The first functional layer may comprise hydrophilic fibers with a lower wetting angle than the protective layer. Here low wetting angle refers to a material being more hydrophobic than a material with a higher wetting angle.
     Foam
   1b. The protective layer may comprise:
     Latex compositions and latex coating
     Polyolefin coating
     Wax coating
     Any suitable coating that is water repellent, for example a hydrophobic coating using one of the above materials.
2. The wrapper comprises the first functional layer sandwiched onto the protective layer:
   2a. The first functional layer may comprise:
     An air-laid tissue
     A nonwoven being spunbond, metlblown or carded
     The first functional layer may comprise hydrophilic fibers with a lower wetting angle than the protective layer.
     A laminate of hydrophobic and hydrophilic cellulose fibers, for example a mix of hydrophobic and hydrophilic cellulose (pulp) fibers
     A mix of synthetic fibers and absorbent fibers, for example polyethylentereftalat (PET) and viscous.
     Foam
     Wadding
   2b. The protective layer may comprise:
     A film or layer of a latex composition or a latex film or layer; Wax coated film or layer; Any suitable film or layer that is water repellent, for example a hydrophobic film using one of the above materials.
     Hydrophobic tissue, polyolefin film or layer
3. The wrapper comprises the first functional layer sandwiched onto the protective layer as in paragraph 1 or 2 above but where the second functional layer is also sandwiched onto the protective layer:
   3a. The second layer may comprise:
     A flexible tissue sheet of microfiber; tissue and/or any of the above described materials or substances for the first protective layer in any suitable form, and both. alone or mixed.

For all above examples 1-3, the protective layer may further comprise:
  Glue; plastic; foam fibers; pulp; etc The protective layer may also comprise a material known from WO 00/76878, the material being air-tight and thus moisture and water tight. The material is in the form of a film produced, at least partially, from one or more polymers such as polyethylene, polypropylene, polyester, polyamide, polyvinyl alcohol or similar polymers, or aluminium foil, aluminium oxide or silicone oxide or the like. The water vapour transmission rate of such a material is maximum 6 $g/m^2$/calendar day according to ASTME 398-83 at 37.8° C. and 90% relative humidity, preferably at most 2 $g/m^2$/calendar day and even more preferably 1 $g/m^2$/calendar day. The material used will also preferably protect a moisture sensitive additive in such a way that said additive will retain their effect for at least 9 months and preferably for 18 month after the packing date. The films may have a thickness of 10-200 micrometer, preferably 20-100 micrometer The protective layer may also comprise a material known from WO 2004/105822 which is suitable for storing an additive in the form of a lacto acid producing bacteria additive. The material is a film-shaped polymer matrix and the additive is embedded in the matrix such that the bacterial cells are protected from moisture thereby increasing the survival of the bacteria.

The polymer matrix may also be used for other additives than lacto acid producing bacteria.

The protective layer may also be an elastic material and a thermoplastic material having the protective qualities according to the above.

The different layers may be attached to each other by any known means, for example, ultrasonic welding, gluing, embossing, etc.

According to the above, the first functional layer may thus be a wiping layer dependent on the material used and/or a transfer layer if there is an additive comprised in the first functional layer. Correspondingly, the second functional layer may be a wiping layer dependent on the material used and/or a transfer layer if there is an additive comprised in the second functional layer.

Here, "wiping layer" refers to the first or second functional layer being used for wiping a surface. The first or second functional layer may be used for wiping if the material is adapted for absorbing or adsorbing a liquid or particles from a surface according to the above.

Here, "transfer layer" refers to the first or second functional layer being used for transferring a substance to a surface. The first or second functional layer may be used for transferring a substance if the first or second functional layer comprises an additive or agent according to the above.

The wrapper may have different shapes and forms in order to improve the packing of the absorbent article. The Wrapper may for example be T-shaped, L-shaped, oval, rectangular, quadratic, triangular, or any other suitable form. The T-shaped form may be used for allowing the wrapper to be used as a release layer both on the backsheet side and on the top sheet side of the absorbent article. This is especially advantageous if the absorbent article is equipped with fastening means in the form of wings, flaps, etc. that comprises an adhesive facing away from the absorbent article. The fastening means will be explained further below.

The wrapper may also comprise an additional wrapper sheet comprising a laminate according to any one of the above described embodiments. The additional wrapper sheet may be a separate sheet or a sheet that is detachably attached to a main wrapper sheet. The main wrapper sheet and the additional wrapper sheet co-operate in wrapping the absorbent article and thus together form the claimed wrapper. The additional wrapper sheet can, for example, be used as a release layer for an adhesive layer. The adhesive layer may be formed on the backsheet for fastening of the absorbent article in an undergarment during use. The adhesive layer also be formed on so called wings or tabs and the wrapper may thus be used as a release layer also in this embodiment.

Here, adhesive refers to any sticky matter that can bond an absorbent article to an undergarment.

Here, wings/tabs/flaps refer to fastening means arranged on and having an extension along longitudinally extending side edges of the absorbent article, which fastening means extend also in a lateral direction with relation to the longitudinally extending side edges. The fastening means are used for folding around the undergarment for attachment to an outside of the undergarment, i.e. the surface of the undergarment that faces away from the user during use. The fastening means may be covered entirely or partly with the adhesive. The fastening means can be made from a number of materials, for example. nonwoven, plastic sheet, film material, laminates of different material, etc. The fastening means may be a part of the backsheet or may be attached to the backsheet or may be attached to any other suitable sheet of the absorbent article. The fastening means may be attached permanently by, for example, welding, gluing, ultrasonic bonding, mechanical bonding etc. The fastening means may also be detachably attached to the absorbent article, for example by use of perforations, glue, welding etc., so that the fastening means may be ripped from the absorbent article before use.

The fastening means are advantageously folded over the topsheet before use, i.e. when positioned in the wrapper. The adhesive on the fastening means then faces away from the absorbent article on the topsheet side of the absorbent article. The additional wrapper may then be used as a release layer, for example by positioning the protective layer against the adhesive. The protective layer and the adhesive layer then have to be chosen so that the adhesive does not stick to the protective layer when removed, but instead remains on the fastening means. The first functional layer is then in this embodiment positioned such that it faces away from the fastening means.

In another embodiment the first or the second functional layer may be positioned against the adhesive layer. In this embodiment the first or second functional layer may be treated, for release purpose, in such a way that the portion of the functional layer lying against the adhesive is treated in a separate way than the remaining portion of the first or second functional layer.

By using a number of wrapper sheets as the wrapper, the different parts of the wrapper cooperate on wrapping the absorbent which gives a neat and simple package at the same time as the user is offered a number of different multifunction wrappers. For example, the user may unwrap the wrapper and the absorbent article so that one part of the wrapper remains protective for one side of the absorbent article so that the absorbent article can be put down on a surface and another part of the wrapper, i.e. the additional wrapper, may be used, for example, for wiping purposes before the absorbent article is freed from the wrapper for use. The remaining part, i.e. e.g. the main wrapper sheet, of the wrapper may be used after the absorbent article has been put in place for use, for example as a hand towel.

The additional wrapper and the main wrapper sheet may not have the same type of functional layers but may be varied within the scope of the claims, and according to the above and below described embodiments.

BRIEF DESCRIPTION OF DRAWINGS

The disclosure will below be described in connection to preferred embodiments and a number of exemplary drawings where;

FIG. 1 schematically shows an absorbent article positioned on a wrapper, according to a first embodiment of the disclosure, being in an unwrapped state;

FIG. 2 schematically shows an absorbent article positioned in a wrapper, according to the disclosure, being in a wrapped state;

FIG. 3 schematically shows a cross-section along line III-III in FIG. 2;

FIG. 4a schematically shows a cross-section along line IV-IV in FIG. 1 of a wrapper comprising the first functional layer and the protective layer according to one embodiment of the disclosure;

FIG. 4b schematically shows a cross-section along line IV-IV in FIG. 1 of a wrapper comprising the first functional layer and the protective layer according to another embodiment of the disclosure;

FIG. 4c schematically shows a cross-section along line IV-IV in FIG. 1 of a wrapper comprising the first functional layer and the protective layer and a second functional layer according to one embodiment of the disclosure, FIG. 4d schematically teaches a perspective view of a wrapper forming a pouch according to one embodiment of the disclosure.

FIG. 5 schematically shows an absorbent article positioned on a wrapper, according to a second embodiment of the disclosure, being in an unwrapped state.

PREFERRED EMBODIMENTS OF THE DISCLOSURE

Figure 6:
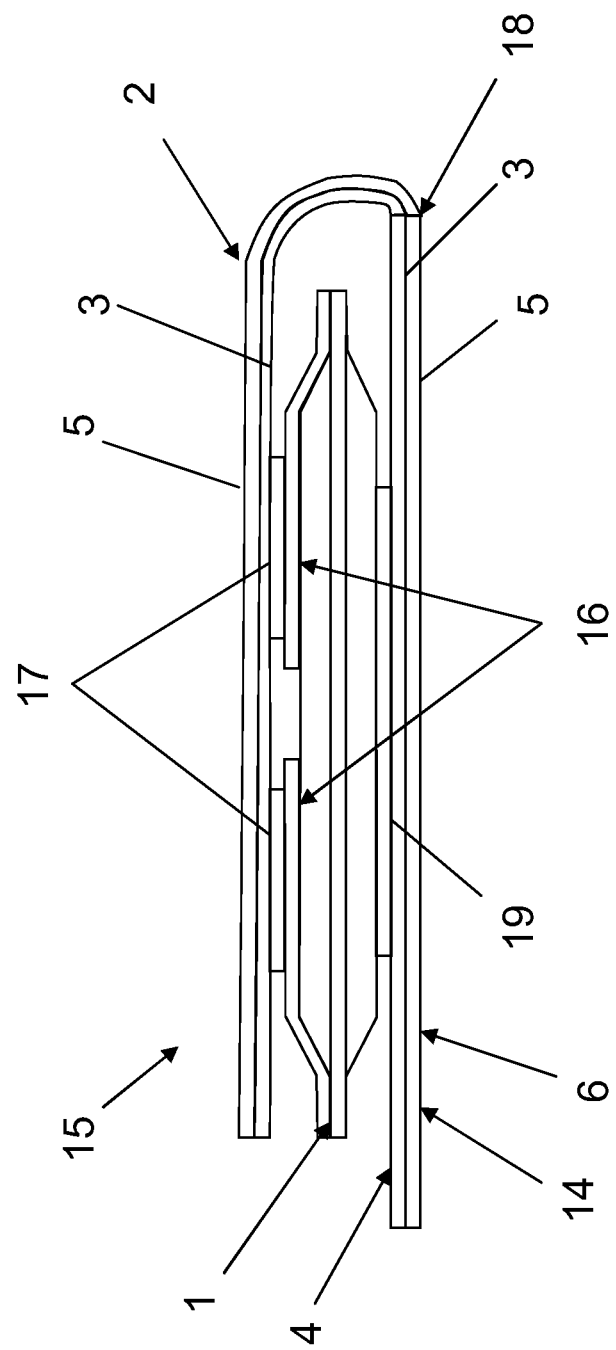
FIG. 6 schematically shows a side view of one embodiment of an absorbent article according to FIG. 5 along line A-A.

FIG. 1 schematically shows an absorbent article 1 positioned on a wrapper 2, according to one embodiment of the disclosure, being in an unwrapped state. In FIG. 1 the absorbent article is positioned on an inner surface 4, hereinafter called the inside 4, of the wrapper 2 facing the absorbent article 1. The wrapper 2 also comprises an outer surface 6, hereinafter called the outside 6, opposite the inner surface 4.

The absorbent article 1 comprises a sandwich structure comprising a liquid pervious topsheet 7, a liquid impervious backsheet 8 facing the inside 4 of the wrapper 2, and an absorbent body 9 therebetween.

The wrapper comprises in the embodiment shown in FIGS. 4a and 4b a first functional layer 3 and a protective layer 5, and in the embodiment shown in FIG. 4c the wrapper 2 comprises also a second functional layer 10.

In FIG. 1 the wrapper 2 is rectangular, but the wrapper may have any shape suitable for being folded over and around the absorbent article 1. The absorbent article 1 may also be positioned in the wrapper 2 in the unfolded state in any position suitable for the wrapper 2 to be folded neatly around the absorbent article 1. The wrapper 2 may thus be folded around the absorbent article 1 in any manner that gives the wrapper 2 a protective feature.

FIG. 2 schematically shows an absorbent article 1 and a wrapper 2, according to FIG. 1, where the absorbent article 1 is positioned in the wrapper 2 and where the wrapper 2 is in a wrapped state. The wrapper 2 encompasses the absorbent article forming a package. The protective layer 5 hinders dirt, moisture and water from entering the package. In FIG. 2 the wrapper and the absorbent article 1 in FIG. 1 have been double folded along a folding line II-II in FIGS. 1 and 2. In FIG. 2 the wrapper has been secured in its folded state by double folded side edges 11 having been attached to each other. The wrapper 2 may be secured in its folded state by any known attachment means, for example adhesive such as glue or the like, or by welding such as ultrasonic welding, laser welding, or the like. The wrapper 2 may be in the form of a so called "single wrap" which is a single wrapper 2 containing an absorbent article 1 without the wrapper 2 being attached to the absorbent article. The wrapper 2 may also be in the form of a so called "quick wrap" which is a single wrapper 2 containing an absorbent article 1 and where the wrapper 2 is attached to the absorbent article 1 so that it may function as a release layer for an adhesive layer positioned on the backsheet of the absorbent article 1.

FIG. 3 schematically shows a cross-section along line III-III in FIG. 2. FIG. 3 shows that the wrapper 2 is folded such that a part 12 of the wrapper 2 overlaps another part of the wrapper. It is also possible to close the wrapper 2 in any known manner, for example by several overlapping parts or by use of non-overlapping parts, i.e. e.g. by edge-to-edge bonding. In FIG. 3 the wrapper 2 comprises a protective layer 5 and a first functional layer 3 as in FIG. 4a, but the wrapper may be of any of the embodiments described in FIGS. 4b-4d.

FIG. 4a schematically shows a cross-section along line IV-IV in FIG. 1 of the wrapper 2 comprising the first functional layer 3 and the protective layer according to the embodiment in FIG. 3. In FIG. 4a the first functional layer 3 is positioned on the inside 4 of the wrapper 2, i.e. such that the first functional layer 3 faces the absorbent article. The protective layer 5 is thus positioned on the outside 6 of the wrapper 2.

FIG. 4b schematically shows a cross-section along line IV-IV in FIG. 1 of a wrapper 2 comprising the first functional layer 3 and the protective layer 5 according to another embodiment of the disclosure. In FIG. 4b the protective layer 5 faces the absorbent article 1, i.e. is positioned on the inside 4 of the wrapper 2. Accordingly, the first functional layer 3 is positioned on the outside 6 of the wrapper 2.

FIG. 4c schematically shows a cross-section along line IV-IV in FIG. 1 of a wrapper 2 comprising the first functional layer 3 and the protective layer 5 and a second functional layer 10 according to one embodiment of the disclosure. In FIG. 4c the first functional layer 3 is positioned on the inside 4 of the wrapper 2 and the second functional layer 10 is positioned on the outside 6 of the wrapper 2. The protective layer 5 is positioned between the first and second functional layers 3, 10.

FIG. 4d schematically shows a perspective view of a wrapper 2 in an unfolded state with an absorbent article 1 positioned on the inside 4 of the wrapper 2. The wrapper 2 forms a pouch according to one embodiment of the disclosure. The wrapper 2 comprises a loosely attached first functional layer 3 forming a pocket 11 between the protective layer 5 and the first functional layer 3. The user may stick a hand or parts of a hand into the pocket 13 and may use the wrapper 2 as a glove with the first functional layer 3 for wiping or cleaning or any other suitable purpose depending in the material of the first functional layer and dependent on if there is an additive in the first functional layer. The wrapper 2 with the pocket 13 is not limited to the embodiment of the wrapper in FIG. 4a, but may be in the form described in connection to FIG. 4c, i.e. with the protective layer 5 on the inside 4 and the first functional layer 3 on the outside 6. The pocket 13 is in this embodiment still formed between the first functional layer 3 and the protective layer 4 and the first functional layer 3 may be used according to above.

In a further embodiment (not shown), the wrapper 2 with the pocket 13 may comprise also a second functional layer 10 according to FIG. 4c and the pocket 13 may be formed according to above between the first functional layer 3 and the protective layer 5 or between the second functional layer 10 and the protective layer 5, or there may be formed two pockets each formed between the first functional layer 3 and the protective layer 5 and the second functional layer 10 and the protective layer 5.

FIG. 5 schematically shows an absorbent article positioned on a wrapper, according to a second embodiment of the disclosure, being in an unwrapped state. The wrapper 2 in FIG. 5 comprises a main wrapper sheet 14 and an additional wrapper sheet 15. Both the main wrapper sheet 14 and the additional wrapper sheet comprise a wrapper 2 laminate according to any one of the embodiments described in connection to FIGS. 1-4. Hence, each or both first and second wrapper sheets 14, 15 comprise a first functional layer 3 and a protective layer 5 and may also comprise a second functional layer (not shown). In FIG. 5, the additional wrapper sheet 15 is detachably attached to the main wrapper sheet 14 via a tear line 18. The tear line 18 may be in the form of a perforated section allowing a user to tear off the additional wrapper sheet 15 for use as, for example, a hand towel, or cleaning towel or a lotion applier, etc.

The main wrapper sheet 14 and the additional wrapper sheet 15 co-operate in wrapping the absorbent article 1 and together they form the claimed wrapper 2. The wrapper 2 may thus be defined as the main wrapper sheet 14 and the additional wrapper 15. The additional wrapper sheet 15 can, for example, be used as a release layer for an adhesive layer 17, 19. In FIG. 5, a first adhesive layer 17 is formed on fastening means 16.

The fastening means 16 may be in the form of so called wings or tabs or flaps and refer to fastening means arranged on and having an extension along longitudinally X extending side edges 20 of the absorbent article 1, which fastening means extend also in a lateral direction Y with relation to the longitudinally X extending side edges 20. The fastening means 16 are used for folding around the undergarment for attachment to an outside of the undergarment, i.e. to the surface of the undergarment that faces away from the user during use. In FIG. 5, the fastening means 16 are covered partly with the adhesive, but may be covered in its entirety. The fastening means 16 can be made from a number of materials, for example. nonwoven, plastics, film material, and/or laminates of different material. The fastening means 16 may be a part of the backsheet 8 or may be attached to the backsheet 8 or may be attached to any other suitable sheet comprised in the absorbent article 1. The fastening means may be detachably attached to the absorbent article, for example by use of perforations, glue, welding etc., so that the fastening means may be torn from the absorbent article 1 before use. The fastening means 16 may also be attached permanently by, for example, welding, gluing, ultrasonic bonding, mechanical bonding, etc.

The fastening means 16 are advantageously folded over the topsheet 7 before use, i.e. when positioned in the wrapper 2. The first adhesive 17 on the fastening means 16 then faces away from the absorbent article 1 on the topsheet 7 side of the absorbent article 1. The additional wrapper sheet 15 may then be used as a release layer, for example by positioning the protective layer 5 against the first adhesive layer 17. The protective layer 5 and the first adhesive layer 17 then have to be chosen so that the adhesive layer does not stick to the protective layer, but instead remains on the fastening means 16. The first functional layer 3 is then in this embodiment positioned such that it faces away from the fastening means 16. However, in FIG. 5 the situation is the opposite, namely that the protective layer 5 faces outwardly and away from the absorbent article 1 and the first functional layer faces inwardly towards the absorbent article 1.

A second adhesive layer 19 may also be formed on the backsheet 8 for fastening of the absorbent article 1 in an undergarment during use. The wrapper 2, for example the main wrapper sheet 14, then may be used as a release layer according to above.

The wrapper 2 may thus be used as a release layer both on the backsheet 8 and the topsheet 7 by use of the main wrapper sheet 14 and the additional wrapper sheet 15 respectively.

Adhesive refers to any sticky matter that can bond an absorbent article to an undergarment.

By using a number of sheets as the wrapper, the different parts of the wrapper co-operate in wrapping the absorbent which gives a neat and simple package at the same time as the user is offered a number of different multifunction wrappers. For example, the user may unwrap the wrapper and the absorbent article so that one part of the wrapper remains protective for one side of the absorbent article so that the absorbent article can be put down on a surface and another part of the wrapper, i.e. the additional wrapper, may be used, for example, for wiping purposes before the absorbent article is freed from the wrapper and used. The remaining part of the wrapper 2, i.e. the main wrapper sheet 15, may then be used after the absorbent article has been put in position for use, for example as a hand towel.

The additional wrapper sheet 14 and the main wrapper sheet 15 do not have to have the same type of functional layers but may be varied within the scope of the claims, and according to the embodiments described in connection to FIGS. 1-4.

FIG. 6 schematically shows a side view of one embodiment of an absorbent article according to FIG. 5 along line A-A. In FIG. 6, the T-shaped wrapper 2 in FIG. 5 has been folded such that the additional wrapper sheet 15 is folded over the absorbent article 1. The main wrapper sheet 14 is positioned on the other side of the absorbent article 1 which means that the main wrapper sheet 14 and the additional wrapper sheet 15 encloses the absorbent article 1 at least partially. The main wrapper 14 may then be folded so that the absorbent article 1 is completely enclosed within the wrapper 2, for example as shown in FIG. 2.

The additional wrapper sheet 15 may comprise different layers than the main wrapper sheet 16.

In FIG. 6 the main wrapper sheet 14 is used as a release layer against the second adhesive layer 19 which means that the layer facing the second adhesive layer 19 must comprise a material that adheres to the second adhesive layer 19, but which can be releases without the adhesive coming off the absorbent article when the release layer, i.e. the main wrapper sheet 14, is removed. In FIG. 6 the additional wrapper sheet 15 is used as a release layer against the first adhesive layer 17 positioned on the fastening means 16. The additional wrapper sheet 15 must in the same way as the main wrapper sheet 14 be treated to allow the release function.

In FIG. 6, the main wrapper sheet 14 and the additional wrapper sheet 15 comprise a protective layer 5 positioned on the outside of the wrapper 2, i.e. on that face of the wrapper 2 that faces away from the absorbent article when the article is wrapped, and a first functional layer 3 on the opposite side of the wrapper, i.e. on the inside 4. The first functional layer 3 may in this embodiment comprise zones (not shown) that are specially treated in order to allow the above described release function. The zones advantageously have an extension at least of the same size as the first and the second adhesive layers 17, 19 respectively. However, the first functional layer 3 in the additional wrapper sheet 15 may be different from the first functional layer 3 in the main wrapper sheet 14 with regard to material and/or composition, etc. Furthermore, the protective layer 5 in the additional wrapper sheet 15 may be different from the protective layer 5 in the main wrapper sheet 14 with regard to material and/or composition, etc. Yet furthermore, one of or both the main wrapper sheet 14 and additional wrapper sheet 15 may comprise a second functional layer as described in connection to FIGS. 1-5.

Figure 7:
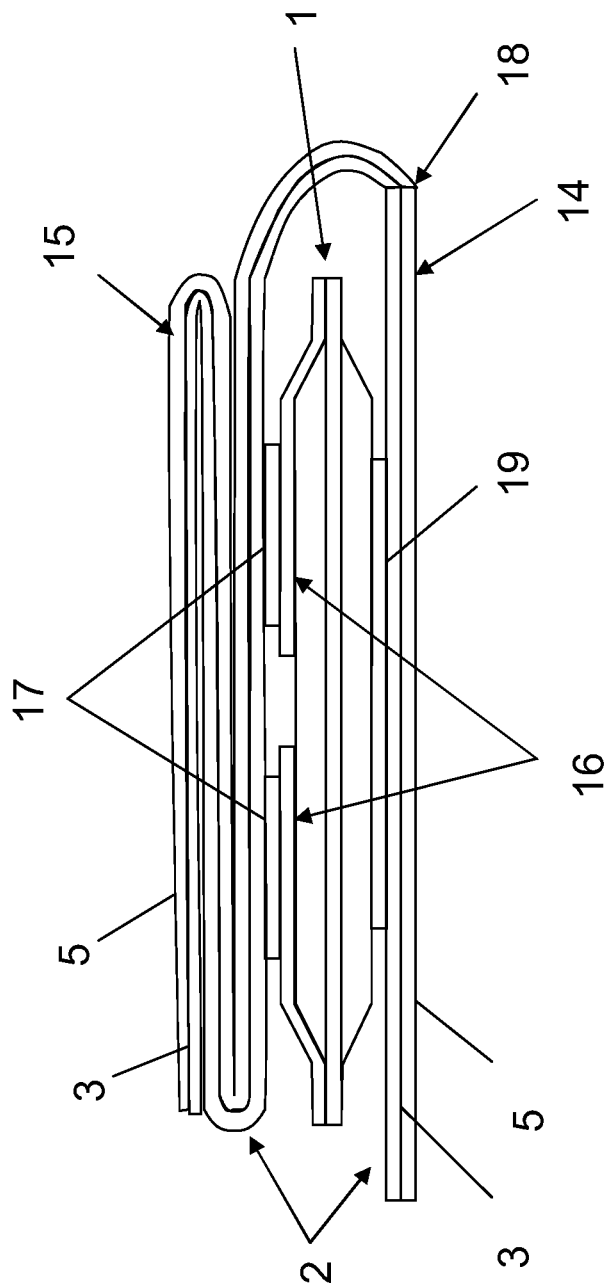
FIG. 7 schematically shows a side view of another embodiment of an absorbent article according to FIG. 5 along line A-A.

FIG. 7 schematically shows a side view of another embodiment of an absorbent article according to FIG. 5 along line A-A. The wrapper 2 in FIG. 7 comprises a main wrapper sheet 14 and an additional wrapper sheet 15 as in FIG. 6, but with the difference that the additional wrapper sheet 15 has been folded over itself a number of times in order to give the user a larger piece of the multi functionality wrapper 2 when the user unfolds the additional wrapper sheet 15 and tears it loose from the main wrapper sheet 14.

Figure 8:
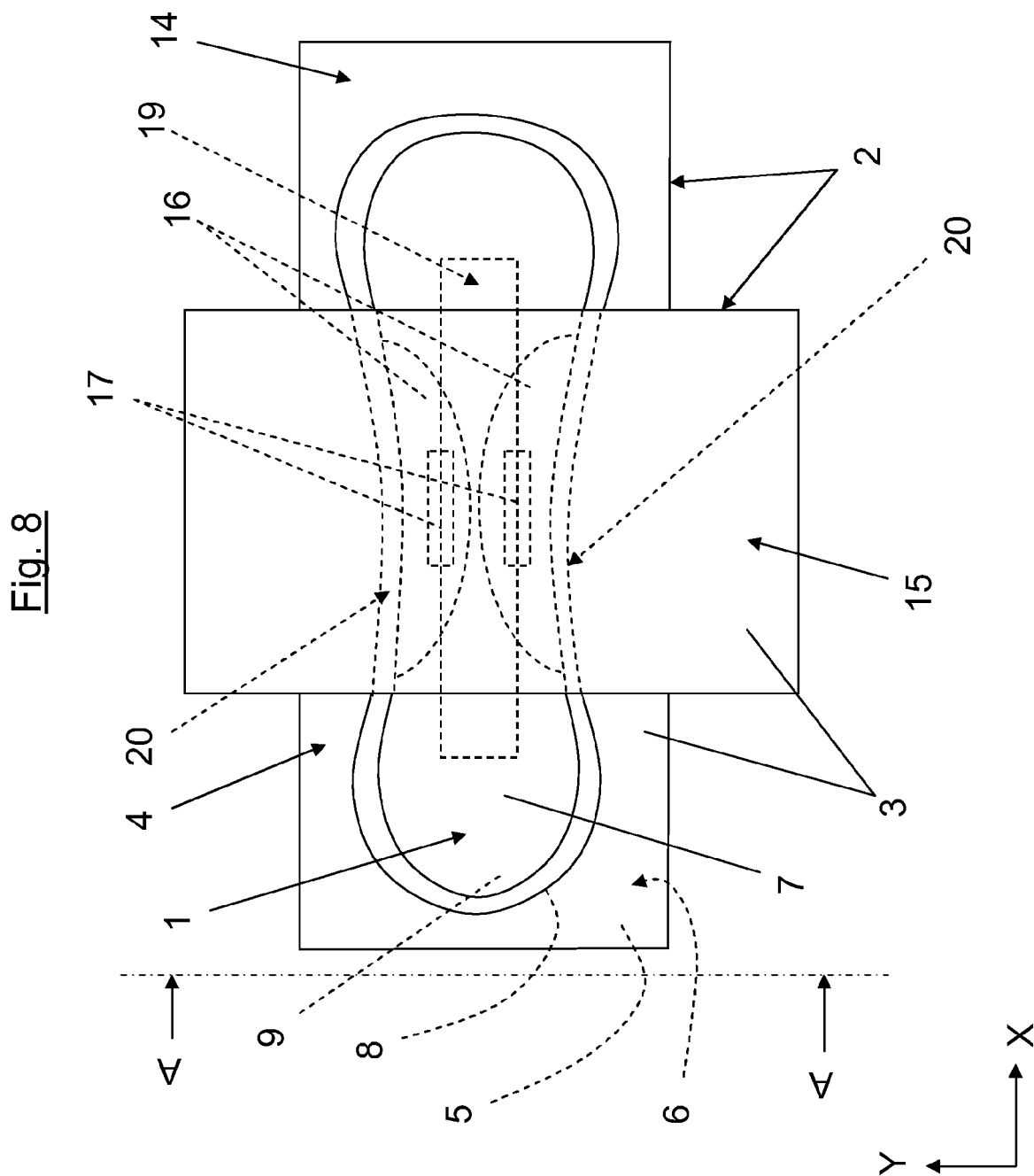
FIG. 8 schematically shows an absorbent article positioned on a wrapper, according to a third embodiment of the disclosure, being in an unwrapped state.

FIG. 8 schematically shows an absorbent article positioned on a wrapper, according to a third embodiment of the disclosure, being in an unwrapped state. The wrapper 2 in FIG. 8 comprises a main wrapper sheet 14 and an additional wrapper sheet 15 as in FIGS. 5-7, but with the difference that the additional wrapper sheet 15 is separated from the main wrapper sheet 15.

Figure 9:
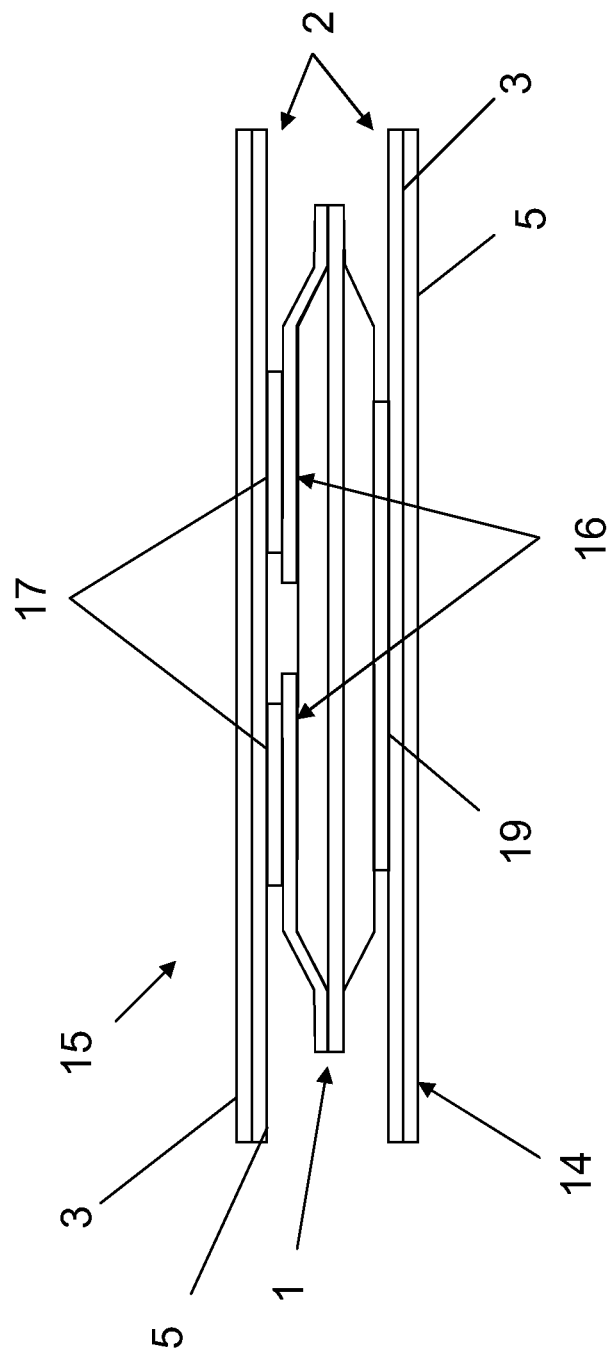
FIG. 9 schematically shows a side view of one embodiment of an absorbent article according to FIG. 8 along line A-A.

FIG. 9 schematically shows a side view of one embodiment of an absorbent article according to FIG. 8 along line A-A. The additional wrapper sheet 15 is positioned over at least a part of the absorbent article 1 and the main wrapper sheet 14 is positioned on the opposite side of the absorbent article 1. Both the main wrapper sheet 14 and the additional wrapper sheet 15 may be used as a release layer for the second and the first adhesive layer 19, 17 respectively. When the user unwraps the packet comprising the absorbent article 1 the user can use the multi functionality additional wrapper sheet 15 in addition to the main wrapper sheet 14. The total amount of multi functionality wrapper 2 is thereby increased.

Figure 10:
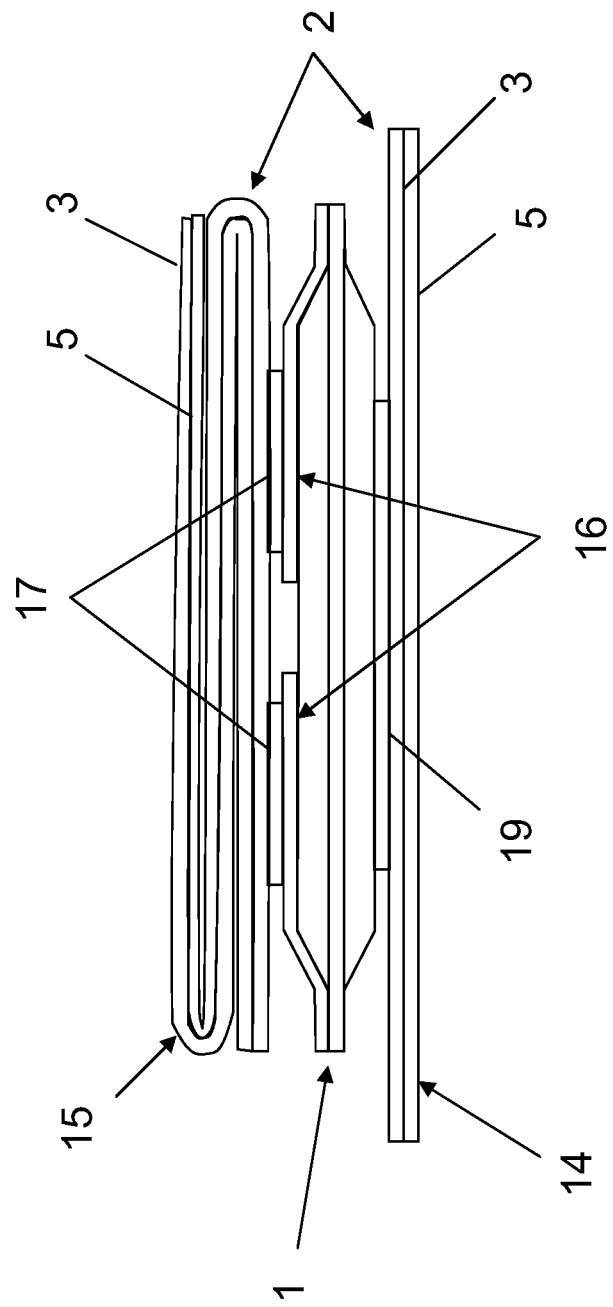
FIG. 10 schematically shows a side view of another embodiment of an absorbent article according to FIG. 8 along line A-A.

FIG. 10 schematically shows a side view of one embodiment of an absorbent article according to FIG. 8 along line A-A. The wrapper 2 in FIG. 10 comprises a main wrapper sheet 14 and an additional wrapper sheet 15 as in FIG. 9, but with the difference that the additional wrapper sheet 15 has been folded over itself a number of times in order to give the user a larger piece of multi functionality wrapper 2 when the user unfolds the additional wrapper sheet 5.

Figure 11:
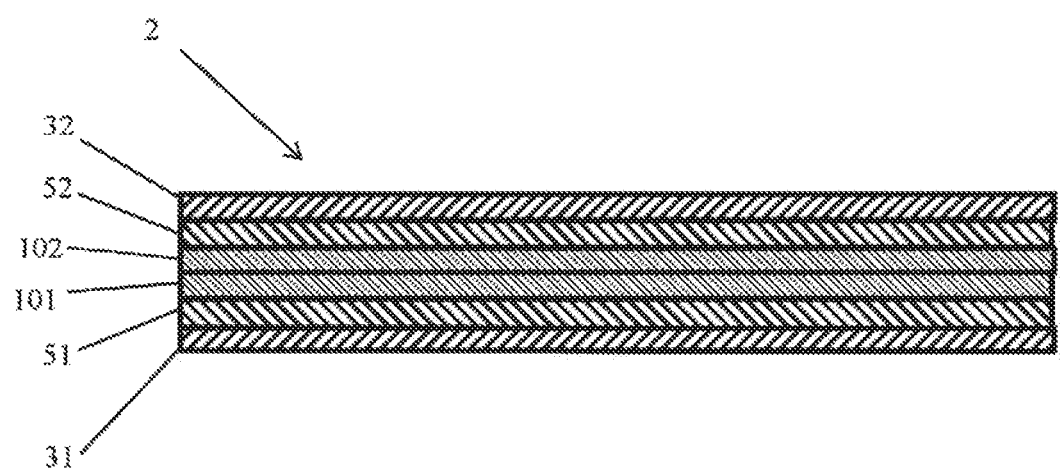
FIG. 11 schematically shows a side view of one embodiment of a wrapper for an absorbent article.

In FIG. 11, the wrapper 2 may also comprise two separating layers 101,102 between two protective layers 51,52. The two layers 101,102 separate the two protective layers 51,52. The separating layers 101,102 may be attached in the wrapper 2 so that the wrapper 2 may be split into two units between the separating layers. A first unit comprises a first functional layer 31, a first protective layer 51 and a first separating layer 101; a second unit comprises a second functional layer 32, a second protective layer 52, and a second separating layer 102. The separating layers 101,102 may be attached to the protective layers 51,52 only partly and separated so that each unit comprises a pocket that can be used for using each unit as a glove.

The invention should not be considered as limited by the above description; rather the scope and limitations of the invention are defined by the enclosed claims, and equivalents thereof. For example, the wrapper may comprise a number of additional wrapper sheets in addition to the main wrapper sheet for wrapping the absorbent article. The main wrapping sheet and the additional wrapping sheets does not have to be used as release layers, but may be used solely as a part of the wrapper. The first functional layer need not be facing the absorbent article when the article is packed, but may face the article or may be sandwiched layer between the first and second functional layer.

The invention claimed is:

1. A packed absorbent article comprising a packing wrapper and an absorbent article enclosed therein, the packing wrapper comprising:
    a first protective layer,
    a first functional layer attached to the first protective layer, wherein the first functional layer is positioned on a face of the wrapper facing the absorbent article or on a face of the wrapper facing away from the absorbent article, and
    a first separating layer attached to the first protective layer,
    a second protective layer,
    a second functional layer attached to the second protective layer, wherein the second functional layer is positioned on an opposite side of the wrapper with reference to the first functional layer,
    a second separating layer attached to the second protective layer,
    wherein the first functional layer is a wiping layer adapted for absorbing or adsorbing a liquid or particles from a surface and/or a transfer layer adapted for transferring a substance to a surface,
    wherein the second functional layer is a wiping layer adapted for absorbing or adsorbing a liquid or particles from a surface and/or a transfer layer adapted for transferring a substance to a surface,
    wherein the two separating layers are sandwiched between the two protective layers and the two separating layers separate the two protective layers from each other so that the wrapper may be split into two units, a first unit comprising the first functional layer, the first protective layer and the first separating layer and a second unit comprising the second functional layer, the second protective layer and the second separating layer,
    wherein, in the first unit, the protective layer and the first functional layer form separate layers removably attached to each other,
    wherein the absorbent article comprises a liquid pervious topsheet, a liquid impervious backsheet and an absorbent body between the topsheet and the backsheet, and
    wherein the packing wrapper has a surface larger than an entire surface of the absorbent article in a flat state.

2. The packed absorbent article according to claim 1, wherein the second separating layer is attached at edge portions thereof to the second protective layer thereby forming a pocket between the second separating layer and the second protective layer, so that the second unit is adapted to be used as a glove.

3. A packed absorbent article comprising a packing wrapper and an absorbent article enclosed therein,
    the wrapper comprising:
        a protective layer, and
        a first functional layer attached to the protective layer,
        wherein the first functional layer is positioned on a face of the wrapper facing the absorbent article or on a face of the wrapper facing away from the absorbent article,
        wherein the first functional layer is a wiping layer adapted for absorbing or adsorbing a liquid or particles from a surface and/or a transfer layer adapted for transferring a substance to a surface, wherein the protective layer and the first functional layer form separate layers removably attached to each other, wherein the absorbent article comprises a liquid pervious topsheet, a liquid impervious backsheet and an absorbent body between the topsheet and the backsheet, and wherein the packing wrapper has a surface larger than an entire surface of the absorbent article in a flat state.

4. The packed absorbent article according to claim 3, wherein the wrapper comprises a main wrapper sheet and an additional wrapper sheet which is detachably attached to the main wrapper sheet via a tear line, one of the main wrapper sheet and the additional wrapper sheet comprising:

the protective layer, and the first functional layer attached to the protective layer, the other of the main wrapper sheet and the additional wrapper sheet, in its entirety, not comprising the protective layer and first functional layer.

5. The packed absorbent article according to claim 3, wherein the first functional layer is positioned on the face of the wrapper facing the absorbent article.

6. The packed absorbent article according to claim 3, comprising a single absorbent article or a plurality of absorbent articles or a number of absorbent articles each being packed in the wrapper.

7. The packed absorbent article according to claim 3, wherein the protective layer is water and/or moisture impermeable and/or has low friction and is dirt repellent.

8. The packed absorbent article according to claim 3, wherein the protective layer is made from an air-tight material being moisture and water impermeable.

9. The packed absorbent article according to claim 3, wherein the protective layer is made from an elastic material and/or a thermoplastic material.

10. The packed absorbent article according to claim 3, wherein the absorbent article has a protective release layer positioned on the liquid pervious topsheet of the absorbent article or only a part of the wrapper constitutes the first functional layer and the first functional layer is positioned against the liquid impervious backsheet of the absorbent article.

11. The packed absorbent article according to claim 3, wherein the means of attachment is ultrasonic welding, gluing, or embossing.

12. A packed absorbent article comprising a packing wrapper and an absorbent article enclosed therein, wherein the packing wrapper comprises:

a protective layer, a first functional layer attached to the protective layer, and a second functional layer attached to the protective layer, wherein the first functional layer is positioned on a face of the wrapper facing the absorbent article or on a face of the wrapper facing away from the absorbent article, wherein the first functional layer is a wiping layer adapted for absorbing or adsorbing a liquid or particles from a surface and/or a transfer layer adapted for transferring a substance to a surface, wherein the protective layer and the first functional layer form separate layers removably attached to each other, wherein the second functional layer is positioned on an opposite side of the wrapper with reference to the first functional layer, wherein the second functional layer is a wiping layer adapted for absorbing or adsorbing a liquid or particles from a surface and/or a transfer layer adapted for transferring a substance to a surface, wherein the absorbent article comprises a liquid pervious topsheet, a liquid impervious backsheet and an absorbent body between the topsheet and the backsheet, and wherein the packing wrapper has a surface larger than an entire surface of the absorbent article in a flat state.

13. The packed absorbent article according to claim 12, wherein the protective layer and the second functional layer form separate layers attached to each other.

14. The packed absorbent article according to claim 12, wherein the protective layer is coated onto the second functional layer, wherein the protective layer cannot be supported by its own structure.

15. The packed absorbent article according to claim 12, wherein the first or second functional layer comprises an active substance for treatment of a body.

16. The packed absorbent article according to claim 12, wherein the first or second functional layer comprises an active substance suitable for cleaning surfaces.

17. The packed absorbent article according to claim 12, wherein the first or second functional layer comprises the active substance in an encapsulated unit.

18. The packed absorbent article according to claim 12, wherein the wrapper comprises the laminate comprising the release layer laminated onto the first and/or the second functional layer.

19. A packed absorbent article comprising a packing wrapper and an absorbent article enclosed therein, wherein the packing wrapper comprises:

a protective layer, and a first functional layer attached to the protective layer, wherein the first functional layer is positioned on a face of the wrapper facing the absorbent article or on a face of the wrapper facing away from the absorbent article, a second functional layer attached to the protective layer, wherein the second functional layer is positioned on an opposite side of the wrapper with reference to the first functional layer, wherein the first functional layer is a wiping layer adapted for absorbing or adsorbing a liquid or particles from a surface and/or a transfer layer adapted for transferring a substance to a surface, wherein the second functional layer is a wiping layer adapted for absorbing or adsorbing a liquid or particles from a surface and/or a transfer layer adapted for transferring a substance to a surface, wherein the protective layer and the first functional layer form separate layers removably attached to each other, wherein the second functional layer is attached at edge portions thereof to the protective layer thereby forming a pocket between the protective layer and the second functional layer, wherein the absorbent article comprises a liquid pervious topsheet, a liquid impervious backsheet and an absorbent body between the topsheet and the backsheet, and wherein the packing wrapper has a surface larger than an entire surface of the absorbent article in a flat state.

20. The packed absorbent article according to claim 19, wherein the pocket is adapted to be turned inside out and to store the absorbent article in an inverted pocket after use.

21. The packed absorbent article according to claim 19, wherein the packing wrapper is adapted to be used as a glove which allows a user to stick a hand or parts of hand into the pocket.

\* \* \* \* \*